(12) United States Patent
Suenaga et al.

(10) Patent No.: US 12,227,725 B2
(45) Date of Patent: Feb. 18, 2025

(54) CELL CULTURING METHOD AND DEVICE (71) Applicant: TOYO SEIKAN GROUP HOLDINGS, LTD., Tokyo (JP)

(72) Inventors: Ryo Suenaga, Yokohama (JP); Maki Mitsuishi, Yokohama (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 1171 days.

(21) Appl. No.: 16/960,816

(22) PCT Filed: Jan. 4, 2019

(86) PCT No.: PCT/JP2019/000011
§ 371 (c)(1),
(2) Date: Jul. 8, 2020

(87) PCT Pub. No.: WO2019/138956
PCT Pub. Date: Jul. 18, 2019

(65) Prior Publication Data
US 2020/0354662 A1    Nov. 12, 2020

(30) Foreign Application Priority Data
Jan. 9, 2018   (JP) .................................. 2018-001091

(51) Int. Cl.
*C12N 5/00* (2006.01)
*C12M 1/00* (2006.01)
*C12M 3/06* (2006.01)

(52) U.S. Cl.
CPC ............ *C12M 23/14* (2013.01); *C12M 23/50* (2013.01); *C12M 27/16* (2013.01); *C12M 29/26* (2013.01); *C12N 5/0068* (2013.01); *C12N 2513/00* (2013.01); *C12N 2527/00* (2013.01)

(58) Field of Classification Search
None
See application file for complete search history.

(56) References Cited

U.S. PATENT DOCUMENTS

| | | | |
|---|---|---|---|
| 2007/0238122 A1* | 10/2007 | Allbritton | C12M 47/04 435/325 |
| 2009/0252749 A1 | 10/2009 | Leister et al. | |
| 2010/0136680 A1 | 6/2010 | Chono et al. | |
| 2013/0059383 A1* | 3/2013 | Dijkhuizen Borgart | C12N 5/0075 435/297.2 |
| 2014/0335600 A1 | 11/2014 | Tanaka et al. | |
| 2016/0095279 A1* | 4/2016 | Brown | C12M 23/46 47/66.7 |
| 2016/0208210 A1* | 7/2016 | Kim | C12M 41/40 |
| 2016/0208219 A1* | 7/2016 | Suenaga | C12N 5/0696 |
| 2017/0362559 A1 | 12/2017 | Hata et al. | |
| 2019/0031994 A1 | 1/2019 | Tanaka et al. | |
| 2019/0300835 A1 | 10/2019 | Suenaga et al. | |
| 2020/0318057 A1* | 10/2020 | Hata | C12N 5/00 |

FOREIGN PATENT DOCUMENTS

| | | |
|---|---|---|
| CN | 101528910 B | 9/2013 |
| EP | 3 015 544 A1 | 5/2016 |
| JP | 2009-011260 A | 1/2009 |
| JP | 2013-158253 A | 8/2013 |
| JP | 2013-247926 A | 12/2013 |
| JP | 2014-023540 A | 2/2014 |
| JP | 2015-008667 A | 1/2015 |
| JP | 2016-086774 A | 5/2016 |
| JP | 2017-184716 A | 10/2017 |
| TW | I398520 B | 6/2013 |
| WO | 2016/121292 A1 | 8/2016 |
| WO | 2016/208526 A1 | 12/2016 |
| WO | 2017/170335 A1 | 10/2017 |
| WO | 2018/230544 A1 | 12/2018 |

OTHER PUBLICATIONS

Machine Translation of Japanese Publication 2009-11260 published Jan. 22, 2009 (previously cited Jul. 8, 2020).
Machine Translation of Japanese Publication No. 2014-23540 published Feb. 6, 2014 (previously cited Jul. 8, 2020).
Machine Translation of Japanese Publication No. 2013-247926 published Dec. 12, 2013 (previously cited Jul. 8, 2020).
International Preliminary Report on Patentability with the translation of the Written Opinion in International Application No. PCT/JP2019/000011, issued on Jul. 14, 2020.
Machine Translation of WO 2018/230544, published Dec. 20, 2018 (previously cited Jul. 8, 2020).
International Search Report for PCT/JP2019/000011 dated Apr. 2, 2019 [PCT/ISA/210].
Extended European Search Report dated Sep. 3, 2021 from the European Patent Office in corresponding EP Application No. 19738819.2.

* cited by examiner

Primary Examiner — Emily A Cordas
(74) Attorney, Agent, or Firm — Sughrue Mion, PLLC (57) ABSTRACT

A cell culturing method and device that uses a cell culture bag (1) that includes a bag body (2) configured from an upper surface film (21) and a lower surface film (22) having a sealed periphery, and a port (3) attached to the bag body (2), and a plurality of recesses (4) being formed in the lower surface film (22). The method including: a closing-off step for closing off the plurality of recesses (4) using the upper surface film (21) by discharging a culture medium (S) contained in the bag body (2) through the port (3); and a releasing step for releasing, in some or all of the plurality of closed-off recesses (4), cells or cell aggregates adhering to the inner surfaces of the recesses (4).

8 Claims, 8 Drawing Sheets

CELL CULTURING METHOD AND DEVICE

CROSS REFERENCE TO RELATED APPLICATIONS

This application is a National Stage of International Application No. PCT/JP2019/000011 filed Jan. 4, 2019, claiming priority based on Japanese Patent Application No. 2018-001091 filed Jan. 9, 2018.

TECHNICAL FIELD

The present invention relates to a cell culturing method and device, more specifically, a cell culturing method and device using a cell culture bag provided with a plurality of recesses.

BACKGROUND ART

In recent years, cells (including tissues, microorganisms, viruses and the like) have been required to be efficiently subjected to culture/differentiation induction in large quantities under an artificial environment in fields such as production of a pharmaceutical, gene therapy, regenerative medicine and immunotherapy In such cell culture, in order to avoid a risk of contamination, a closed-system cell culture bag is used in several cases. The cell culture bag is configured from: a bag body configured from a plastic film having a sealed periphery; and a port attached to the bag body, for example. Patent Document 1 describes a cell culture bag in which movement of cells in the cell culture bag is suppressed by providing a plurality of recesses in a bottom surface of a bag body.

However, in cell culture, generally, if a cell concentration in a culture medium excessively increases with proliferation of cells, growth of the cells is inhibited by exhaustion of a medium component required for the proliferation, accumulation of metabolites of the cells per se, or the like, whereby proliferation efficiency of cells is reduced, and on the other hand, even if the cell concentration in the culture medium is excessively low, proliferation/differentiation induction efficiency of cells is reduced. Therefore, in order to improve culture/differentiation induction efficiency of cells, it is necessary to maintain the cell concentration in a proper range.

Also when spheroid culture is performed using the cell culture bag provided with the plurality of recesses, it is necessary to maintain the cell concentration in the proper range in each recess, and therefore the cells are inseminated in each recess so that the number of cells in each recess may be uniformized.

Further, in such spheroid culture, in order to form a spheroid (cell aggregate) having a uniform and appropriate size in each recess, it is required that the spheroid is formed one by one in each recess to maintain one spheroid per recess until completion of culture.

In order to form one spheroid in one recess, cell low adhesion treatment according to which the cells become hard to adhere to an inner surface of the cell culture bag is preferably applied to gather the cells to a bottom center of a spherical crown-shaped recess of the cell culture bag. Specific examples of the cell low adhesion treatment include treatment of coating a phospholipid polymer, a polyvinyl alcohol derivative, a surfactant or protein such as albumin, or the like to inhibit cell adhesive protein from adsorbing onto a surface of a plastic film.

RELATED ART DOCUMENTS

Patent Documents

Patent Document 1: JP-A-2009-11260

DISCLOSURE OF THE INVENTION

Problems to be Solved by the Invention

Figure 10:
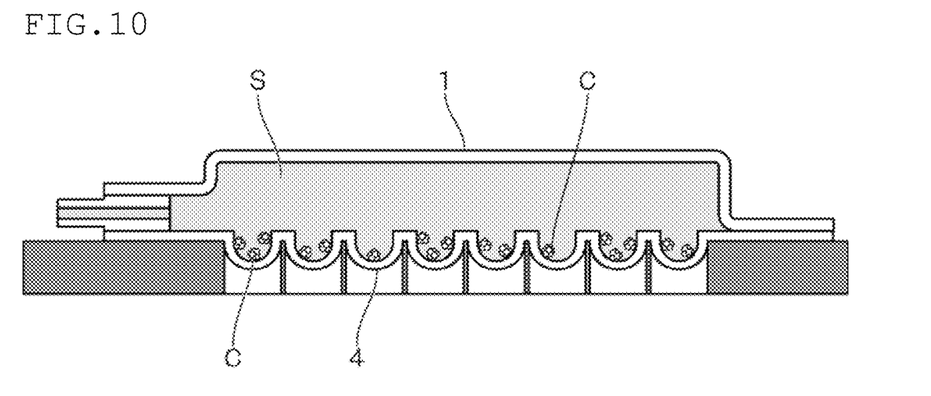
FIG. 10 is a schematic cross-sectional view of a cell culture bag to show a state in which cells adhere to a plurality of places of inner surfaces of recesses of the cell culture bag.

However, even if cell low adhesion treatment is applied to a cell culture bag, cells or spheroids adhere to inner surfaces of recesses due to various factors such as treatment unevenness, and adhesion force of cultured cells and the like in several cases. For example, as shown in FIG. 10, cells C inseminated to each recess 4 of a cell culture bag 1 containing a culture medium S adhere to a plurality of places on the inner surfaces of the recesses 4 by cell adhesive protein in several cases. In the case, each cell C forms a spheroid with an adhered position as a starting point, and therefore a plurality of small spheroids are formed in one recess 4. Then, the spheroids adhering to the inner surfaces of the recesses 4 do not move, and therefore the spheroids cannot adhere to each other to form one spheroid.

Therefore, in order to form the spheroid one by one in each recess, it is necessary to release the cells adhering to the plurality of places on the inner surface of the recess to gather the cells in one place (for example, a bottom center) in the recess.

Moreover, even when the spheroid is formed one by one in each recess, the spheroid adheres to the inner surface of the recess in several cases. In a part of the spheroids adhering to the inner surface of the recess, a medium component is easily exhausted and metabolites are easily accumulated, and therefore proliferation/differentiation induction efficiency of cells in a whole of the spheroids is reduced.

Therefore, in spheroid culture, in order to improve the proliferation/differentiation induction efficiency of cells, it is required to release the spheroids adhering to the inner surfaces of the recesses on a regular basis (for example, when replacing the culture medium) to change adhesion positions of the spheroids.

If cell culture using a conventional well plate is performed, the cells (for example, the cells immediately after insemination or the cells forming the spheroids) adhering to the inner surface of the well can be released by causing a jet flow in the culture medium in the well (recess) by means of a pipette. Specifically, a tip of the pipette is inserted into the well, and the culture medium is gently sucked up while preventing the cells from being sucked, and then the culture medium sucked up is forcefully injected into the well to cause the jet flow, and the cells can be released by the jet flow.

However, in cell culture using the cell culture bag, it is difficult to insert the pipette into the recess in the cell culture bag while maintaining a closed system.

Figure 11:
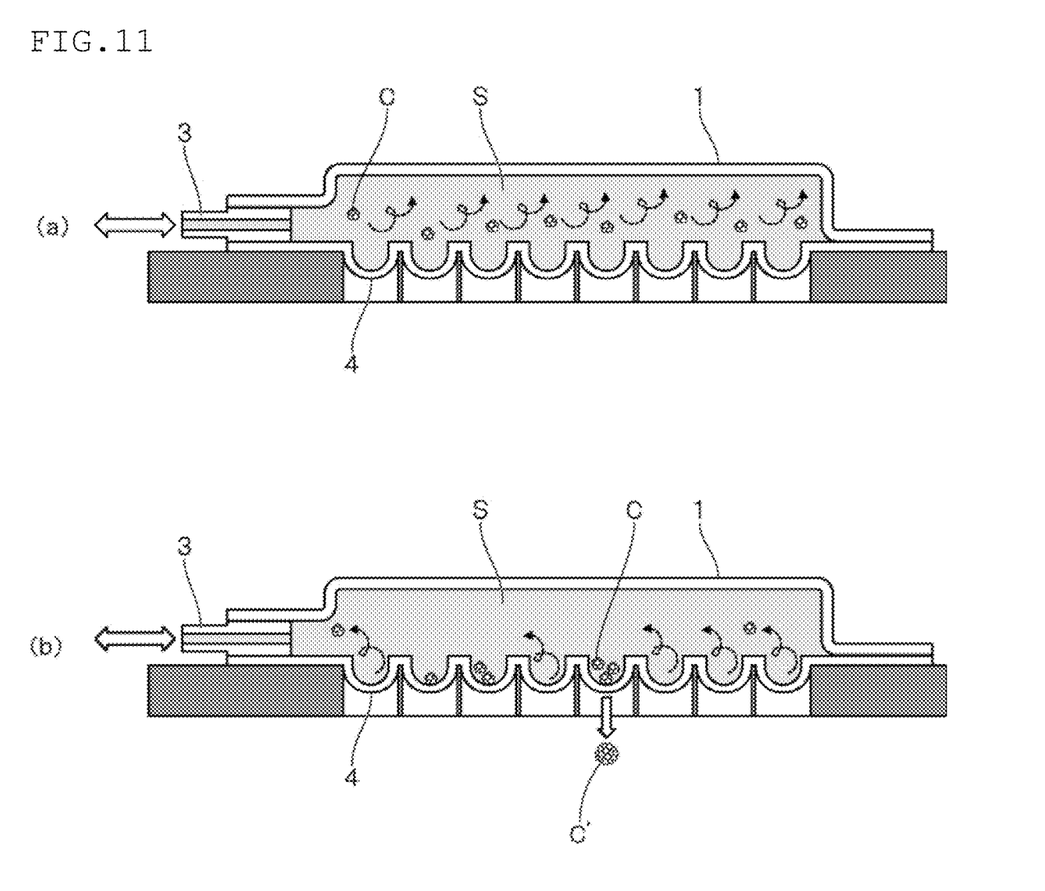
FIG. 11(a) is a schematic cross-sectional view of a cell culture bag to show a state in which spheroids are released from recesses in the cell culture bag.
FIG. 11(b) is a schematic cross-sectional view of the cell culture bag to show a state in which released spheroids move between the recesses in the cell culture bag.

In this connection, in the cell culture using the cell culture bag, as shown in FIG. 11(*a*), a method of strongly injecting the culture medium S through a port 3 to cause a water flow of the culture medium S in the cell culture bag 1 to release the cells C adhering to inner walls of the recesses 4 can be considered.

However, in this method, as shown in FIG. 11(*b*), the cells C precipitated in the recesses 4 and the cells C released move to other recesses 4 to cause non-uniformity of the cell concentrations in the recesses 4. In particular, if a great number of cells C enter in one recess 4, the cells C are eventually formed into an excessively large aggregate C' to reduce the proliferation/differentiation induction efficiency of cells.

The present invention has been made in view of the above-described circumstances, and an objective of the present invention is to provide a cell culturing method and device, wherein, when culturing cells using a cell culture bag in which a plurality of recesses are formed, proliferation/differentiation induction efficiency of cells or cell aggregates can be improved by releasing the cells or the cell aggregates adhering to the inner surfaces of the recesses while preventing movement of cells between the recesses.

Means for Solving the Problems

A cell culturing method according to the present invention, using a cell culture bag provided with a bag body configured from upper and lower surface films having a sealed periphery, and a port attached to the bag body, in which a plurality of recesses are formed in the lower surface film, comprising: a closing-off step for closing off the plurality of recesses using the upper surface film by discharging a culture medium contained in the bag body through the port; and a releasing step for releasing, in some or all of the plurality of closed-off recesses, cells or cell aggregates adhering to the inner surfaces of the recesses by providing the recesses with a physical stimulus from an outside of the cell culture bag.

Moreover, a cell culturing device according to the present invention, using a cell culture bag provided with a bag body configured from upper and lower surface films having a sealed periphery, and a port attached to the bag body, in which a plurality of recesses are formed in the lower surface film, comprising a stand having a placement surface on which the cell culture bag is placed; a liquid feed means for discharging a culture medium contained in the bag body through the port until the plurality of recesses are closed off using the upper surface film; and a releasing means for providing, in some or all of the plurality of closed-off recesses, the recesses with a physical stimulus from an outside of the cell culture bag in order to release cells or cell aggregates adhering to the inner surfaces of the recesses.

Advantageous Effects of the Invention

According to a cell culturing method and device according to the present invention, when culturing cells using a cell culture bag in which a plurality of recesses are formed, proliferation/differentiation induction efficiency of cells or cell aggregates can be improved by releasing the cells or the cell aggregates adhering to inner surfaces of the recesses while preventing movement of cells between the recesses.

For example, when the cells adhere to a plurality of places on the inner surfaces of the recesses of the cell culture bag, the proliferation/differentiation induction efficiency of cells can be improved by releasing the cells to gather the cells in one place to efficiently form one cell aggregate (spheroid) in one recess by closing off the recesses and providing the recesses with a physical stimulus while preventing movement of cells between the recesses.

Further, for example, when the cell aggregates adhere to the inner surfaces of the recesses of the cell culture bag, the proliferation/differentiation induction efficiency of cells or cell aggregates can be improved by releasing the cell aggregates to change adhesion sites of the cell aggregates by closing off the recesses and providing the recesses with the physical stimulus while preventing movement of the cell aggregates between the recesses.

MODE FOR CARRYING OUT THE INVENTION

Hereinafter, a preferred embodiment of the present invention will be described with reference to drawings.
(Cell Culture Bag)

First, a cell culture bag used in the present embodiment will be described with reference to FIG. 1 prior to description of a cell culturing device according to the present embodiment. A cell culture bag 1 shown in FIG. 1(a) to FIG. 1(c) is provided with: a bag body 2 configured from an upper surface film 21 and a lower surface film 22 which are stacked to heat seal a periphery 20; and a port 3 attached to this bag body 2. A size of the bag body 2 is not particularly limited, and is preferably adjusted to 50 to 500 mm in length and 50 to 500 mm in width, for example.

Figure 1:
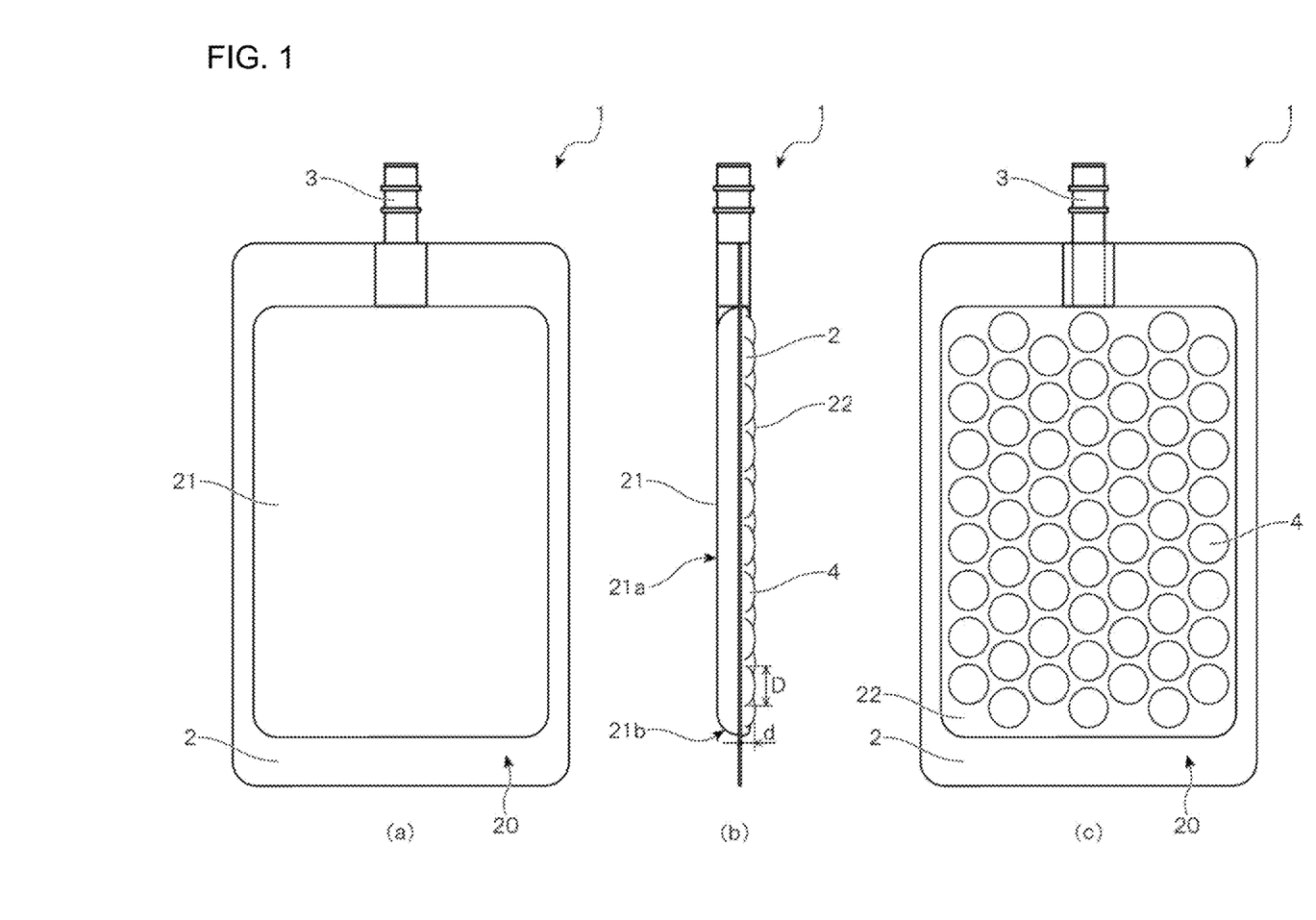
FIG. 1(a) is a plan view schematically showing a cell culture bag used in an embodiment of the present invention.
FIG. 1(b) is a side view schematically showing the cell culture bag used in the embodiment of the present invention.
FIG. 1(c) is a bottom view schematically showing the cell culture bag used in the embodiment of the present invention.

It should be noted that, in each drawing including FIG. 1, illustration of a flow path of a tube connected to the port 3 or the like, and illustration of a closing-off means which closes up the flow path, such as a pinch, a valve and the like are omitted.

As shown in FIG. 1(c), a plurality of recesses 4 each serving as a cell culture portion are formed in the lower surface film 22. An opening diameter (diameter) D of in the recess 4 is preferably 0.3 to 10 mm, and a depth d is preferably 0.1 mm or more, in order to suppress cell movement in the bag body 2 so that the cells under culture may retain in one recess 4. The recesses 4 may be formed into the same opening diameter in all of the recesses 4, or may include two or more kinds of recesses having a different opening diameter. For example, the lower surface film 22 may be divided into a plurality of regions, and the opening diameter of the recess 4 may be differed for each region.

Moreover, in the cell culture bag 1, in order to facilitate gathering of the cells in a bottom of the recess 4, as shown in FIG. 1(b), the recess 4 has a spherical crown shape. It should be noted that the shape of the recess 4 is not limited thereto. For example, the recess 4 may have a shape dented in an earthenware mortar shape (conical shape). In order to facilitate gathering of the cells in the bottom of the recess 4, a ratio d/D of a depth d to a diameter D of the recess 4 is preferably adjusted to 0.05 to 1.

Moreover, the recesses 4 are preferably aligned in a staggered shape as shown in FIG. 1(c) so that an occupied area of the recess 4 in the lower surface film 22 may be as large as possible, but the recesses 4 may be aligned in a lattice shape, when necessary.

As shown in FIG. 1(b), the upper surface film 21 has a swelling shape which is swollen into a plateau shape configured from: a substantially flat top surface part 21a covering an upper part of a whole of the plurality of recesses 4; and an inclined part 21b formed on a circumference of the top surface part 21a. Thus, in comparison with a flat pouch-shaped container prepared only by stacking two plastic films and sealing a periphery, even if the bag body 2 is filled with the culture medium, deformation in which the periphery of the lower surface film 22 is lifted up is suppressed.

The upper surface film 21 and the lower surface film 22 which form the bag body 2 are formed of a plastic film having gas permeability. The gas permeability of this plastic film is preferably 5,000 mL/(m$^2$·day·atm) or more in an oxygen transmission rate measured at a test temperature of 37° C. in accordance with determination of gas-permeability rate in JIS K 7126.

Specific examples of a material to be used in the plastic film which forms the bag body 2 include a thermoplastic resin such as polyethylene, polypropylene, an ethylene-vinyl acetate copolymer, polyester, a silicone-based elastomer, a polystyrene-based elastomer, a tetrafluoroethylene-hexafluoropropylene copolymer (FEP) or the like. The materials may be used in a single layer or by laminating the same kind or different kinds of materials, but if heat sealability upon heat sealing the periphery is taken into consideration, the material preferably has a layer which functions as a sealant layer.

Moreover, a thickness of the plastic film which forms the bag body 2 is preferably 30 to 200 μm at which the film has moderate shape retainability so that the upper surface film 21 may keep the swelling shape while having flexibility, and the lower surface film 22 may keep a shape of the recess 4.

The port 3 is formed of a tubular member through which the medium, the cells or the like can flow, and can be formed of a thermoplastic resin such as polyethylene, polypropylene, vinyl chloride, a polystyrene-based elastomer, FEP or the like, for example.

First Embodiment

Figure 2:
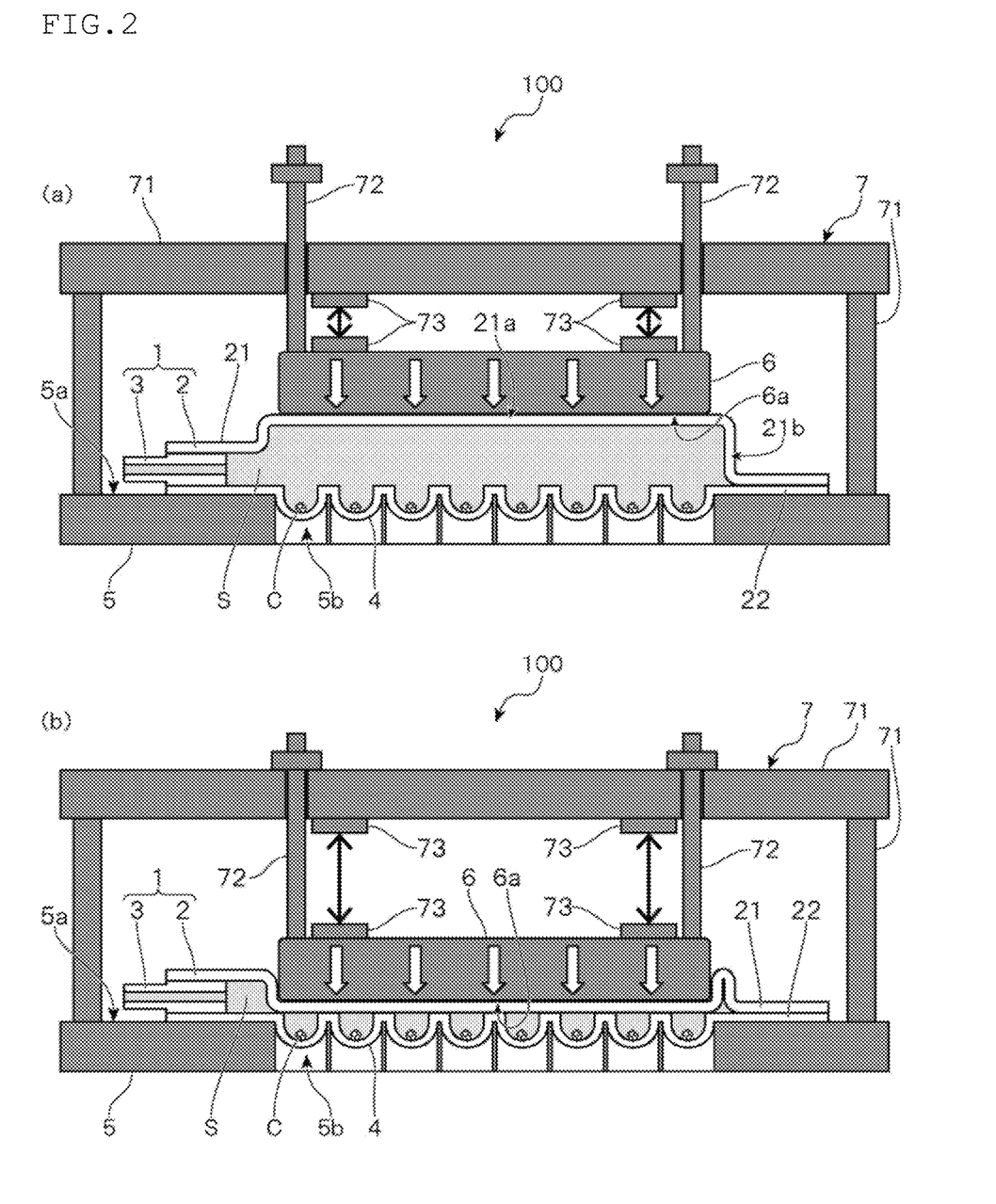
FIG. 2(a) is a schematic cross-sectional view of a cell culturing device according to a first embodiment of the present invention to show a state in which a pressing member is raised.
FIG. 2(b) is a schematic cross-sectional view of the cell culturing device according to the first embodiment of the present invention to show a state in which the pressing member falls.
Figure 3:
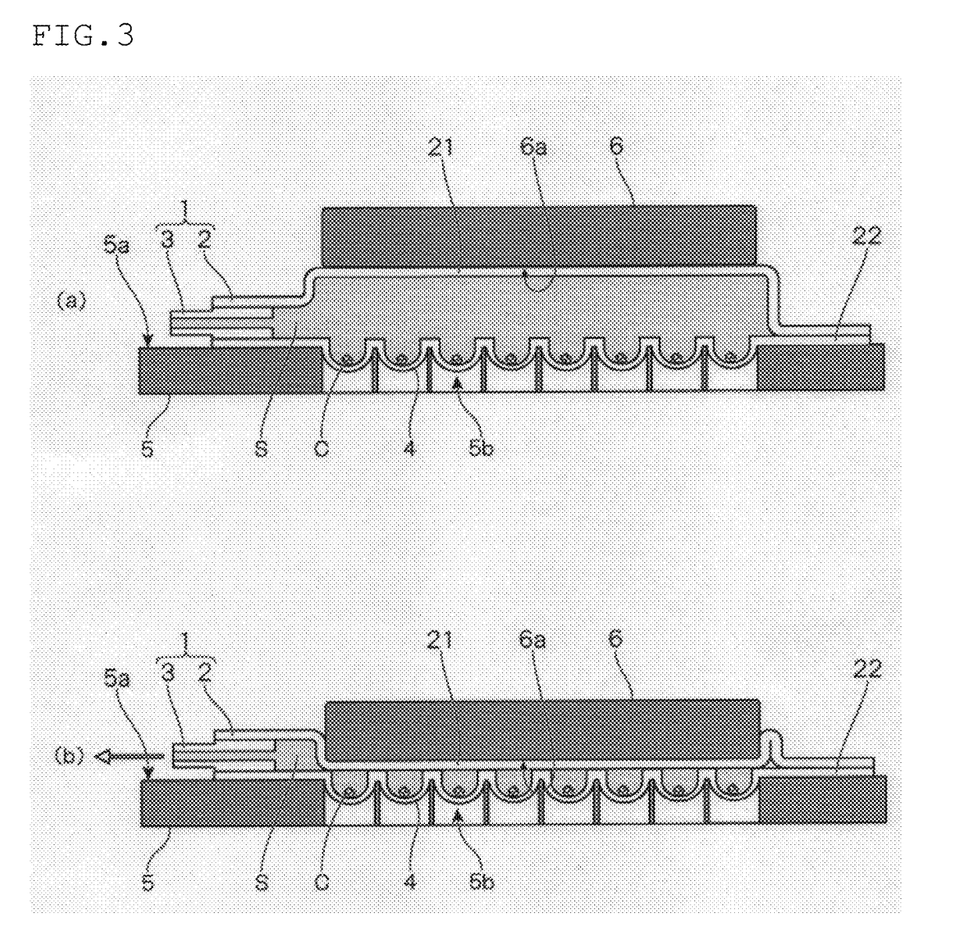
FIG. 3(a) is a schematic cross-sectional view of the cell culture bag to show a state during cell culture in the first embodiment of the present invention.
FIG. 3(b) is a cross-sectional view of the cell culture bag to show a closing-off step in the first embodiment of the present invention.

Next, a cell culturing method and device according to an embodiment of the present invention will be described with reference to FIGS. 2 and 3. FIG. 2 shows a schematic cross-sectional view of a cell culturing device 100 according to a first embodiment, in which FIG. 2(a) shows a state in which a pressing member is raised, and FIG. 2(b) shows a state in which the pressing member falls.

The cell culturing device 100 according to the present embodiment is provided with: a stand 5 on which a cell culture bag 1 is placed; a pressing member 6 having a bottom surface 6a which presses a portion of a top surface part 21a of an upper surface film 21; and a support mechanism 7 which supports the pressing member 6.

In FIG. 2, illustration of a pump as a liquid feed means for injecting and discharging a culture medium through a port 3 of the cell culture bag 1, and a releasing means for releasing spheroids from recesses 4 of the cell culture bag 1 is omitted. Specific examples of the pump include a peristaltic pump connected to the port 3 through a tube.

The liquid feed means is not limited to the pump, and may be a syringe, for example.

The stand 5 has a placement surface 5a on which the cell culture bag 1 is horizontally placed. On this placement surface 5a, an opening 5b is formed as a shape for receiving each of a plurality of recesses 4 formed in a lower surface film 22 of the cell culture bag 1. Thus, the placement surface 5a supports the lower surface film 22 in non-contact with the recesses 4, and therefore flattening and deformation of the recesses 4 are avoided, whereby outflow of the cells in the recesses 4 is prevented, and further gas permeability from the lower surface film 22 is improved.

The shape for receiving each of the plurality of recesses 4 is not limited to the opening, and may be a recess or a wire net shape, for example.

The pressing member 6 is a plate-shaped member having a substantially rectangular planar shape according to the top surface part 21a of the cell culture bag 1, and has a flat bottom surface 6a.

The support mechanism 7 is configured from: a frame 71 provided on the stand 5; guide pins 72 which are extended upward from four corners of an upper surface of the pressing member 6 to penetrate the frame 71 so as to be able to vertically move; and a biasing means 73 which biases the pressing member 6 downward. The biasing means 73 are configured from magnets 73 which are arranged on the upper surface of the pressing member 6, and the frame 71 with the same pole sides facing each other. According to repulsive force applied between the permanent magnets 73, the pressing member 6 vertically moves according to a height of the upper surface film 21.

The biasing means 73 is not limited to the permanent magnet. Moreover, the biasing means 73 may be omitted, and according to self-weight of the pressing member 6, the pressing member 6 may vertically move according to the height of the upper surface film 21.

Confine

Next, the cell culturing method according to the present embodiment will be described with reference to FIGS. 3 and 4. Illustration of the support mechanism 7 of the cell culturing device shown in FIG. 2 is omitted in FIGS. 3 and 4.

As shown in FIG. 3(a), a spheroid C formed during cell culture is contained at a uniform cell concentration in each recess 4.

As shown in FIG. 3(b), in a closing-off step, all of the plurality of recesses 4 are closed off using the upper surface film 21 by discharging a culture medium S contained in a bag body 2 through the port 3 by means of a pump (not shown). The upper surface film 21 is pressed by the flat bottom surface 6a of the pressing member 6, and therefore the upper surface film 21 is flatted, whereby each of the plurality of recesses 4 is securely closed off using the upper surface film 21. Thus, the spheroid C is confined in each recess 4, and therefore in the next releasing step, outflow of the spheroid C from each recess 4 is prevented.

When closing off the plurality of recesses 4 using the upper surface film 21, each recess 4 may be tightly closed or need not be tightly closed. When the plurality of recesses 4 are not tightly closed, the plurality of recesses 4 only need to be closed to such an extent that overflow of the cells from the recesses 4 can be prevented.

Figure 4:
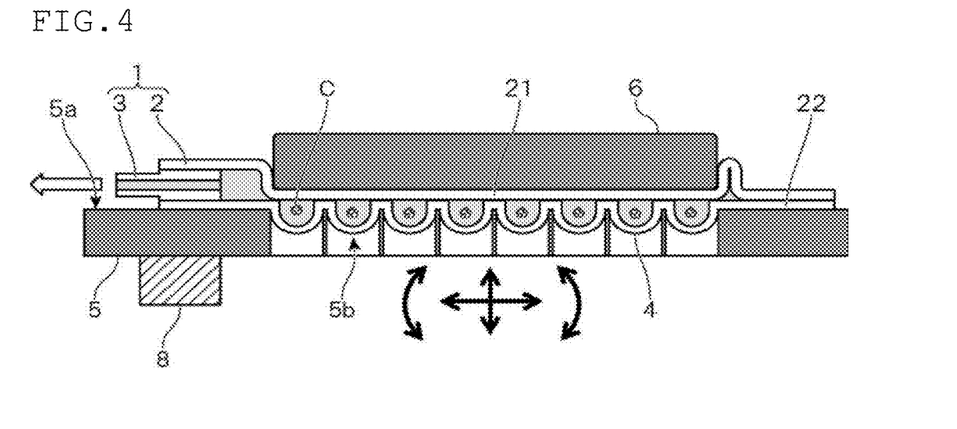
FIG. 4 is a schematic cross-sectional view of the cell culture bag illustrating a releasing step in the first embodiment of the present invention.

Next, as shown in FIG. 4, in the releasing step, the spheroids C are released, in some or all of the plurality of closed-off recesses 4, from inner surfaces of the recesses 4.

In the releasing step, some or all of the plurality of recesses 4 should be provided with vibration or oscillation. In that case, the cell culturing device 100 may be wholly provided with vibration or oscillation, or physical force of vibration or oscillation may be applied to the lower surface film 22 which forms the recesses 4. Vibration or oscillation applied to the recesses 4 is also transmitted to the spheroids C adhering to the inner surfaces of the recesses 4, whereby the spheroids C are released from the inner surfaces of the recesses 4.

It should be noted that, as a means for providing vibration or oscillation, a vibrator 8 attached to the stand 5 of the cell culture device as shown in FIG. 4 may be used, or an oscillation device may be used. Moreover, vibration may be directly applied to the recesses 4 by directly bringing the vibrator into contact with the recesses 4. Moreover, vibration or oscillation may be selectively applied to a part of the recesses 4.

Moreover, vibration or oscillation may be reciprocating motion, or may be rotating motion by a test tube mixer, for example.

Figure 5:
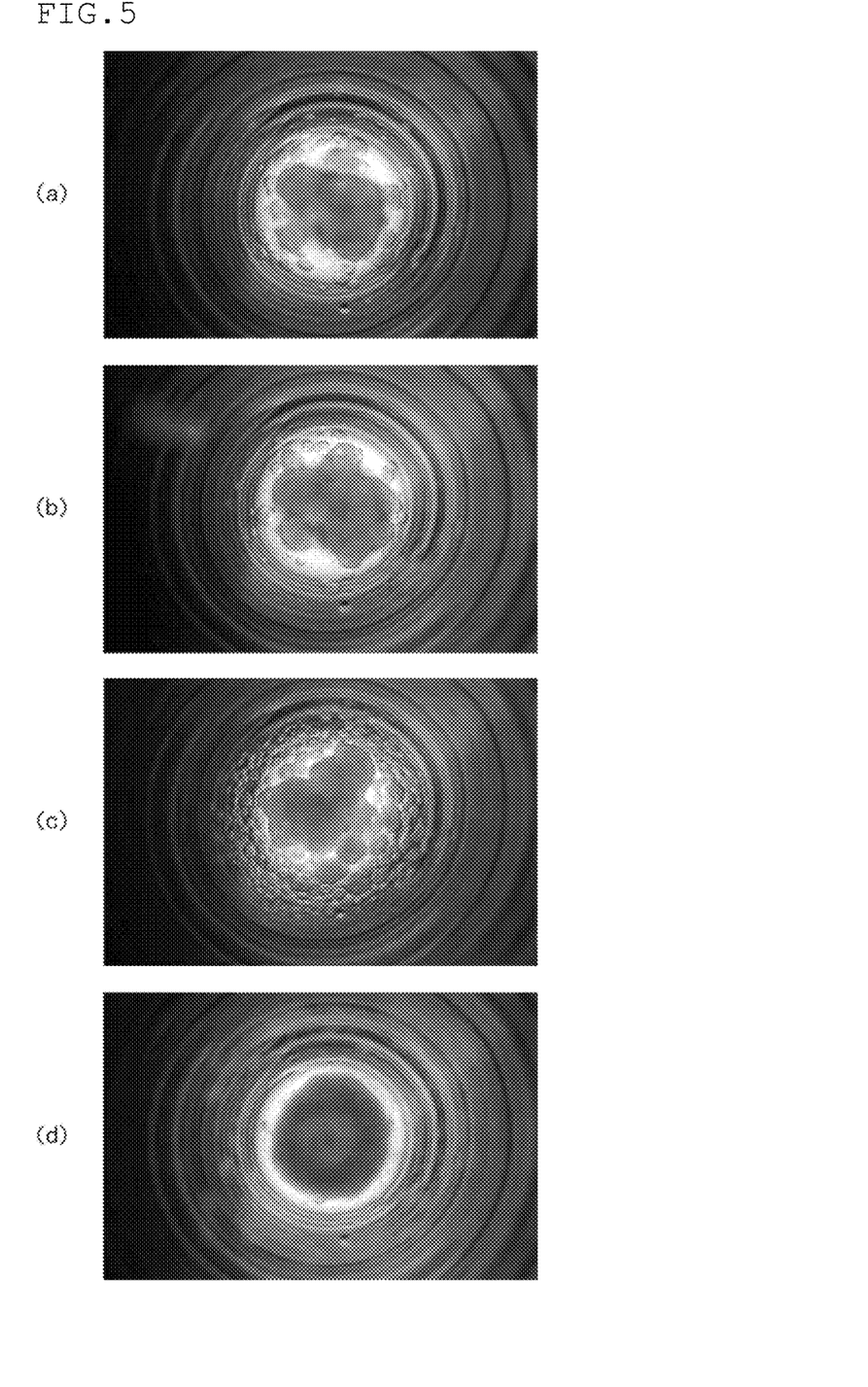
FIG. 5(a) is a photograph showing an inside of one recess to which cells are inseminated to show the inside of the recess after 48 hours from insemination.
FIG. 5(b) is a photograph showing the inside of one recess to which the cells are inseminated to show the inside of the recess after the closing-off step.
FIG. 5(c) is a photograph showing the inside of one recess to which the cells are inseminated to show the inside of the recess immediately after the releasing step.
FIG. 5(d) is a photograph showing the inside of one recess to which the cells are inseminated to show the inside of the recess after 15 hours after the releasing step.

Here, FIG. 5 is a photograph showing an inside of one recess 4 to which the cells are inseminated in the present embodiment. A culture medium (StemFit (registered trademark)) manufactured by Ajinomoto Co., Inc. was used herein, and $3 \times 10^4$ undifferentiated iPS cells (cell strain 1231A3) were inseminated per recess (well).

FIG. 5(a) shows the recess after 48 hours from insemination. As shown in the figure, the cells inseminated adhere not only to a bottom center of the recess but also to every place of the inner surface of the recess to form the spheroids. It should be noted that, in the figure, the spheroids adhering to a circumferential inner surface of the recess are away from a focal plane of the photograph, and therefore do not appear clearly.

FIG. 5(b) shows the recess after the closing-off step. The spheroids still adhere to every place of the inner surface only by closing off the recess 4.

In the closing-off step, the peristaltic pump was used as the liquid feed means, and the culture medium was discharged through the port 3 until the upper surface film 21 closes off each recess 4 at a liquid feed rate of 1.0 mL/min.

FIG. 5(c) shows the recess immediately after the releasing step. The stand 5 was vibrated using the vibrator 8. As shown in the figure, a great number of small spheroids released from the circumferential inner surface of the recess 4 gather in the bottom center of the recess.

In the releasing step, the test tube mixer 8 being the vibrator 8 was used as the releasing means. Then, as shown in FIG. 4, each recess 4 of the cell culture bag 1 was provided with a physical stimulus from outside by pressing the test tube mixer 8 to a lower surface of the stand 5 of the cell culturing device 100 for one minute. As the test tube mixer 8, horizontal vibration type PresentMixer 6076881 having a vibration rate of about 2800 revolutions per minute, manufactured by TIETECH Co., Ltd., was used.

FIG. 5(d) shows the recess after 15 hours from the releasing step. After the releasing step, the culture medium was injected into the bag body 2 and culture was resumed. As shown in the figure, one spheroid is formed in the bottom center of the recess 4.

Thus, according to the present embodiment, the spheroids are released from the inner surface and gathered in one place while preventing movement of spheroids between the recesses. Thus, proliferation/differentiation induction efficiency of spheroids can be improved by efficiently forming one spheroid in one recess 4.

Further, even if one spheroid is formed in one recess 4, when the spheroids adhere to the inner surfaces of the recesses 4, the proliferation/differentiation induction efficiency of spheroids can be improved by closing off the recesses 4 again and providing the recesses 4 with the physical stimulus, and releasing the spheroids from the inner surfaces to change adhesion sites of the spheroids while preventing movement of the spheroids between the recesses 4.

Second Embodiment

Figure 6:
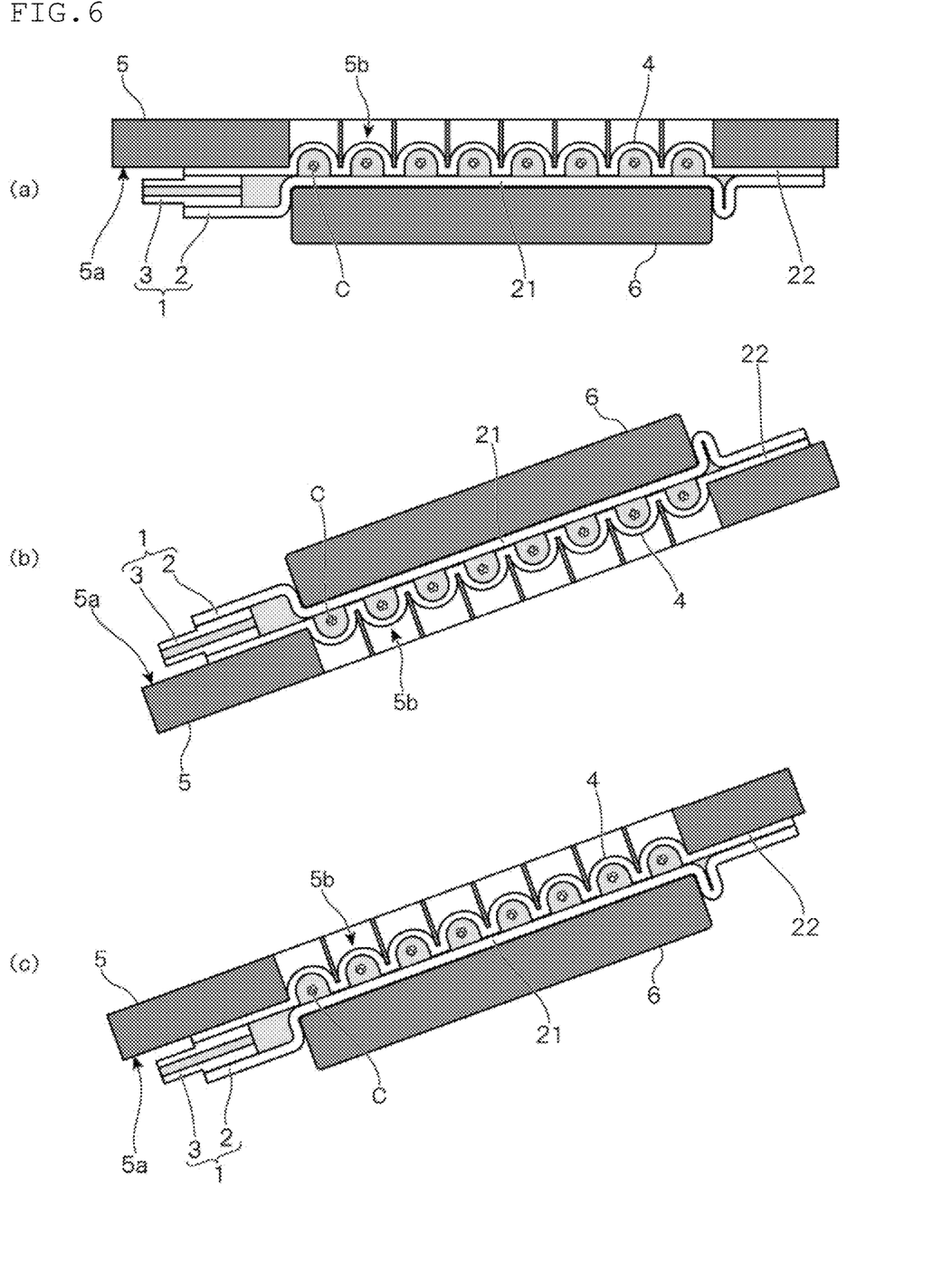
FIG. 6(a) is a schematic cross-sectional view of a cell culture bag illustrating a second embodiment of the present invention to show a vertically inverted cell culture bag.
FIG. 6(b) is a schematic cross-sectional view of the cell culture bag illustrating the second embodiment of the present invention to show an inclined cell culture bag.
FIG. 6(c) is a schematic cross-sectional view of the cell culture bag illustrating the second embodiment of the present invention to show a vertically inverted and inclined cell culture bag.

Next, a second embodiment of the present invention will be described with reference to FIG. 6. In the figure, illustration of the same components as in the first embodiment is partly omitted.

In the present embodiment, after the closing-off step described in the first embodiment, in a releasing step, as shown in FIG. 6(a), a cell culture bag 1 is vertically inverted together with the cell culturing device 100 shown in FIG. 1 while closing off each recess 4, in place of providing the recesses 4 of the cell culture bag with the physical stimulus from outside.

Moreover, as shown in FIG. 6(b), in the releasing step, the cell culture bag 1 may be inclined together with the cell culturing device 100 shown in FIG. 1 while closing off each recess 4 in place of providing the recesses of the cell culture bag with the physical stimulus from outside. An inclination angle of the cell culture bag 1 relative to a horizontal line is not particularly limited, and the cell culture bag 1 may be inclined up to 90 degrees, for example.

Further, as shown in FIG. 6(c), in the releasing step, the cell culture bag 1 may be vertically inverted and inclined together with the cell culturing device 100 shown in FIG. 1 while closing off each recess 4, in place of providing the recesses with the physical stimulus from outside.

Thus, in the present embodiment, spheroids C adhering to the inner surfaces of the recesses 4 are released due to gravity by a simple operation of vertically inverting and/or inclining the culturing bag 1. Moreover, each recess 4 is closed off using an upper surface film 21, and therefore movement of released cells or spheroids C to other recesses 4 is avoided.

Moreover, the present embodiment is preferable when the cells and the aggregates adhering to the inner surfaces of the recesses 4 of the cell culture bag 1 are released only by vertically inverting and/or inclining the cell culture bag 1.

The cell culture bag 1 may be vertically inverted and/or inclined manually, or may be vertically inverted and/or inclined by a mechanism of a robot arm and the like.

Moreover, in the releasing step of the first embodiment described above, the cell culture bag 1 may be further vertically inverted and/or inclined as in the present embodiment. Moreover, also in the releasing step in third and fourth embodiments described later, the cell culture bag 1 may be further vertically inverted and/or inclined as in the present embodiment.

Third Embodiment

Next, a third embodiment of the present invention will be described with reference to FIG. 7. In the figure, illustration of the same components as in the first embodiment is partly omitted.

In the present embodiment, after the closing-off step described in the first embodiment, in a releasing step, each recess 4 is provided with a physical stimulus by thrusting up each recess from below by means of a thrust-up member 9 arranged below each of a plurality of recesses 4, in place of providing the recesses 4 of the cell culture bag with vibration or oscillation.

The thrust-up member 9 vertically moves in an opening 5b formed on a placement surface 5a of a stand 5 by means of an actuator (not shown). A bottom of a crown spherical recess 4 curved in a protrusion shape downward is thrusted up by means of the thrust-up member 9, whereby swelling is inverted so as to be curved in the protrusion shape upward. The spheroids C adhering to the inner surfaces of the recesses 4 are released by thrusting up the recesses 4.

When the recess 4 remains in an inverted state upward, an original crown spherical shape curved in the protrusion shape downward can be recovered, for example, by injecting a culture medium into a bag body 2 next time, and then pressing the bag body 2 by means of a pressing member 6 or the like to increase internal pressure of the bag body 2. Moreover, the shape of the recess 4 can be recovered also by sucking the recess 4 inverted upward from below, for example.

Figure 7:
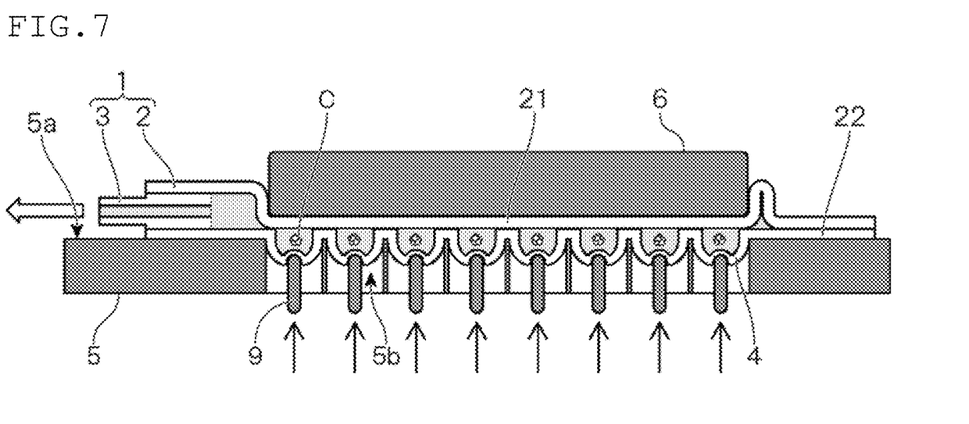
FIG. 7 is a schematic cross-sectional view of a cell culture bag illustrating a releasing step of a third embodiment of the present invention.

An example in which the thrust-up members 9 simultaneously thrust up all of the recesses 4 is shown in FIG. 7, but the thrust-up members may selectively thrust up a part of the recesses 4.

Moreover, one thrust-up member 9 may sequentially thrust up the recesses 4 one by one. In that case, the actuator (not shown) should be configured in such a manner that the actuator not only vertically moves the thrust-up member 9, but also moves the thrust-up member in a horizontal direction to sequentially position the thrust-up members below desired recesses 4.

Moreover, the recesses 4 may be provided with the physical stimulus by thrusting up the recesses 4 by means of the thrust-up members 9 and simultaneously applying vibration or oscillation to a cell culture bag 1 to release the spheroids C adhering to the inner surfaces of the recesses 4.

Thus, even in cell culture using the cell culture bag 1, adhesion positions of the spheroids C can be changed in the recesses 4 while preventing movement of the spheroids C between the recesses 4.

Thus, culture/differentiation induction efficiency of cells can be improved.

Fourth Embodiment

Figure 8:
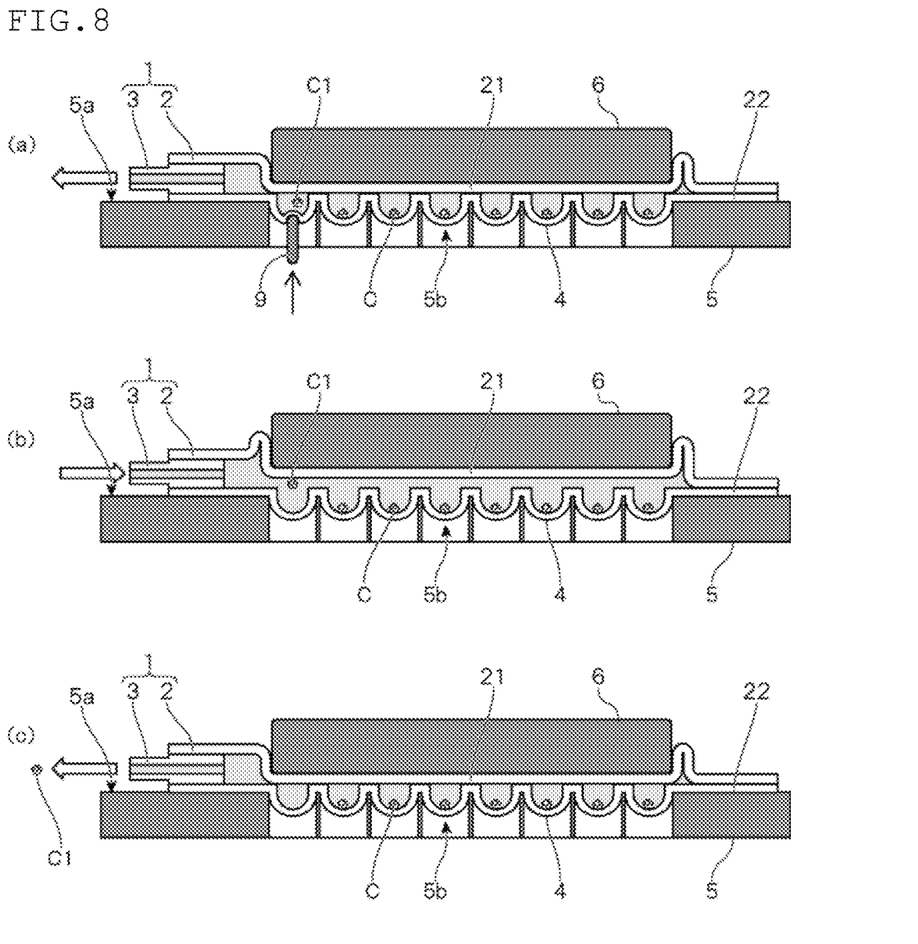
FIG. 8(a) is a schematic cross-sectional view of a cell culture bag illustrating a cell culturing method according to a fourth embodiment of the present invention to show a releasing step.
FIG. 8(b) is a schematic cross-sectional view of the cell culture bag illustrating the cell culturing method according to the fourth embodiment of the present invention to show a clearing step.
FIG. 8(c) is a schematic cross-sectional view of the cell culture bag illustrating the cell culturing method according to the fourth embodiment of the present invention to show a discharging step.

Next, a cell culturing method and device according to a fourth embodiment of the present invention will be described with reference to FIG. 8.

A structure of the cell culturing device according to the present embodiment can be formed in the same manner as in the second embodiment. In the present embodiment, after the closing-off step described in the first embodiment, unnecessary spheroids C1 are selectively released and eliminated.

As shown in FIG. 8(a), in a releasing step, spheroids C1 in a part of a plurality of closed-off recesses 4 are selectively released. Also in the present embodiment, the same releasing means as in the first embodiment is used.

Next, as shown in FIG. 8(b), in a clearing step, closing-off of the recesses 4 using an upper surface film 21 is cleared by injecting a culture medium into a bag body 2 through a port 3 by means of a pump. As a result of clearing closing-off of the recesses 4, released spheroids C1 are formed into a state of allowing outflow to an outside of the recesses 4.

Next, as shown in FIG. 8(c), in a discharging step, the selectively released spheroids C1 are discharged together with the culture medium S by discharging the culture medium in the bag body 2 through the port 3 by means of the pump. Thus, unnecessary spheroids C1 can be selectively released and removed.

While the unnecessary spheroids C1 are selectively released and removed, the spheroids C which are not selected in other recesses 4 adhere to the inner surface of each recess 4, and therefore are not discharged through the port 3.

It should be noted that, in the present embodiment, the unnecessary spheroids C1 are selected, but the spheroids to be selected are not limited to the unnecessary spheroids, and may be selected as an extraction sample, for example. Moreover, the spheroids in two or more recesses 4 can also be selectively released.

Fifth Embodiment

Figure 9:
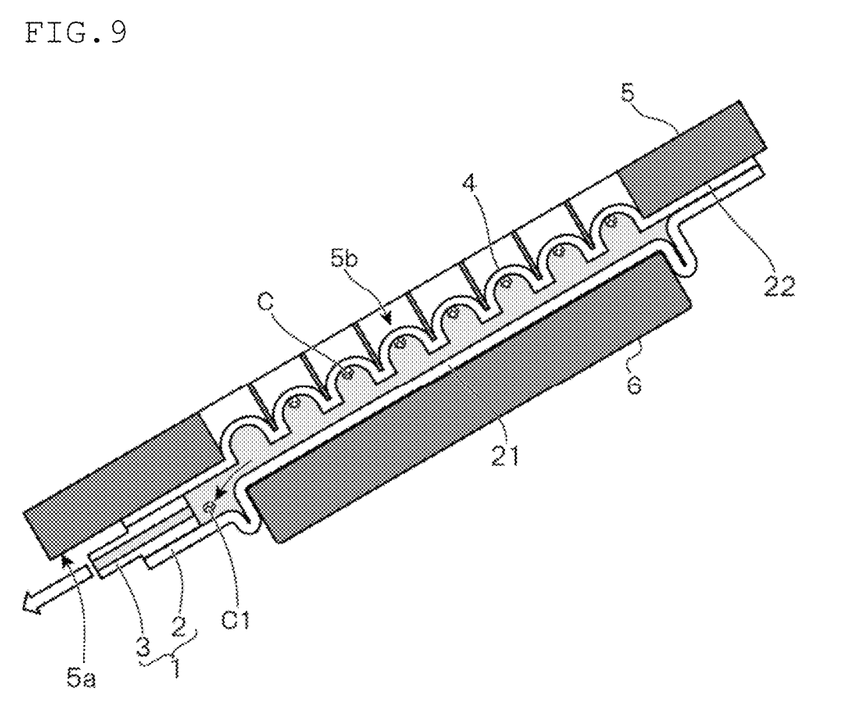
FIG. 9 is a schematic cross-sectional view of a cell culture bag illustrating a cell culturing method according to a fifth embodiment of the present invention.

Next, a fifth embodiment of the present invention will be described with reference to FIG. 9.

A structure of a cell culturing device according to the present embodiment can be formed in the same manner as in the fourth embodiment.

In the present embodiment, in the discharging step described in the fourth embodiment, selectively released spheroids C1 are discharged together with a culture medium S through a port 3 to an outside of a bag body 2 in a state in which a cell culture bag 1 is vertically inverted and inclined so that the port 3 may be located below a plurality of recesses 4.

The released spheroids C1 may be discharged together with the culture medium S through the port 3 to the outside of the bag body 2 in a state in which the cell culture bag 1 is only vertically inverted without being inclined.

Moreover, the present embodiment is preferable when the cells and the aggregates adhering to inner sides of the recesses 4 of the cell culture bag 1 are not released only by vertically inverting the cell culture bag 1.

Moreover, an operation of vertically inverting and/or inclining the cell culture bag 1 may be performed in the discharging step, or may be performed in a stage previous to the discharging step.

Thus, the selectively released spheroids C1 in the releasing step move to the outside of the recesses 4 by vertically inverting the cell culture bag 1, and easily discharged through the port 3. Further, if the cell culture bag 1 is inclined so that the port 3 may be located below the plurality of recesses 4, the released spheroids C1 can be further easily discharged through the port 3.

As described above, the present invention is described by showing preferred embodiments, but the present invention is not limited to the embodiments described above, and various modifications can be obviously made within the scope of the present invention. In the above-described embodiment, a rod-like thrust-up member is used, but a shape of the thrust-up member is not limited thereto. Moreover, in the above-described embodiment, an example of pressing the upper surface film by means of the pressing member is described, but the pressing member may be omitted in the present invention.

Moreover, in the above-described embodiment, an example of releasing the spheroids adhering to the inner surface of the cell culture bag is described, but the present invention can be applied also to a case where the cells not forming the spheroids are released from the inner surfaces of the recesses of the cell culture bag.

INDUSTRIAL APPLICABILITY

The present invention can be used as a technology on efficiently culturing various cells.

The entire contents of the documents described in the description concerning the present application and the description of the Japanese application serving as a basis of claiming the priority concerning the present application to the Paris Convention are incorporated by reference herein.

EXPLANATION OF NUMERICAL SYMBOLS

1 Cell culture bag
2 Bag body
20 Periphery
21 Upper surface film
21a Top surface part
21b Inclined part
22 Lower surface film
3 Port
4 Recess (well)
5 Stand
5a Placement surface
5b Opening
6 Pressing member
6a Bottom surface
7 Support mechanism
71 Frame
72 Guide pin
73 Biasing means (magnet)
8 Vibrator (test tube mixer)
9 Thrust-up member
100 Cell culturing device
C, C, C1 Cells or cell aggregates (spheroids)
S Culture medium

The invention claimed is:

1. A cell culturing method using a cell culture bag comprising a bag body configured from upper and lower surface films having a sealed periphery, and a port attached to the bag body, wherein a plurality of recesses are formed in the lower surface film, and wherein cells or cell aggregates are cultured in the plurality of recesses, comprising:
   a closing-off step comprising pressing the upper surface film from above by means of a pressing member having a flat bottom surface, wherein during the pressing a culture medium contained in the bag body is discharged through the port such that the plurality of recesses are closed off by the upper surface film to confine the cells or the cell aggregates being cultured in each recess wherein the upper surface film is not in contact with the cells or cell aggregates;
   a releasing step comprising releasing, in some or all of the plurality of recesses closed-off by the upper surface film, the cells or the cell aggregates adhering to inner surfaces of the recesses from inner surfaces of the recesses to change adhesion positions of the cells or the cell aggregates in each recess; and
   a further culturing step comprising culturing the cells or the cell aggregates released from the inner surfaces of the recesses in each recess.

2. The cell culturing method according to claim 1, wherein the cells or the cell aggregates adhering to the inner surfaces of the recesses are released in some or all of the plurality of recesses closed-off by the upper surface film by providing the recesses with a physical stimulus from outside of the cell culture bag in the releasing step.

3. The cell culturing method according to claim 2, wherein vibration or oscillation is provided in some or all of the plurality of recesses closed-off by upper surface film in the releasing step.

4. The cell culturing method according to claim 2, wherein some or all of the plurality of recesses closed-off by the upper surface film are thrusted up from outside in the releasing step.

5. The cell culturing method according to claim 1, wherein the cell culture bag is vertically inverted and/or inclined in the releasing step.

6. The cell culturing method according to claim 1, wherein the cells or the cell aggregates in a part of the plurality of recesses are selectively released in the releasing step, the cell culturing method further comprising, subsequent to the releasing step:

a clearing step comprising injecting the culture medium into the bag body through the port to separate the upper surface film from the lower surface film such that the plurality of recesses closed off by the upper surface film are cleared; and a discharging step comprising discharging the cells or the cell aggregates selectively released in the releasing step through the port to the outside of the bag body together with the culture medium.

7. The cell culturing method according to claim 6, wherein the cells or the cell aggregates selectively released are discharged through the port to the outside of the bag body together with the culture medium, in a state in which the cell culture bag is vertically inverted, in the discharging step.

8. The cell culturing method according to claim 7, wherein the cells or the cell aggregates selectively released are discharged through the port to the outside of the bag body together with the culture medium, in a state in which the cell culture bag is inclined so that the port may be located below the plurality of recesses, in the discharging step.

\* \* \* \* \*